United States Patent [19]
Rothenberg

[11] Patent Number: 5,352,414
[45] Date of Patent: Oct. 4, 1994

[54] INCUBATOR UNIT AND FILTER SYSTEM

[76] Inventor: Barry E. Rothenberg, P.O. Box 977, Del Mar, Calif. 92014-0977

[21] Appl. No.: 998,425

[22] Filed: Dec. 30, 1992

[51] Int. Cl.[5] ............................................. B01L 11/00
[52] U.S. Cl. ..................................... 422/101; 422/99; 422/102; 422/104; 435/311; 435/313; 435/809
[58] Field of Search ............... 422/101, 104, 159, 102, 422/99; 435/311, 312, 313, 316, 800, 809, 298; 55/316, 387, 485, 524, 385.1, 385.2, 385.4, 478

[56] References Cited

U.S. PATENT DOCUMENTS

| | | | |
|---|---|---|---|
| 3,576,721 | 4/1971 | Mason | 435/809 |
| 3,886,047 | 5/1975 | Billups, Jr. | 195/139 |
| 3,944,403 | 3/1976 | Simpson et al. | 55/316 |
| 3,966,422 | 6/1976 | Waters | 55/316 |
| 4,111,807 | 9/1978 | Boomus et al. | 210/152 |
| 4,336,329 | 6/1982 | Hesse et al. | 435/3 |
| 4,604,110 | 8/1986 | Frazier | 55/74 |
| 4,793,922 | 12/1988 | Morton | 210/317 |
| 4,935,371 | 6/1990 | Rickloff | 435/296 |
| 5,047,348 | 9/1991 | Stinson | 435/311 |
| 5,066,597 | 11/1991 | Stinson et al. | 435/311 |
| 5,081,017 | 1/1992 | Longoria | 435/30 |

OTHER PUBLICATIONS

Cole-Parmer 1993-1994 Catalog, pp. 1392, 1396, and 1400-1402.

Primary Examiner—Lyle A. Alexander
Assistant Examiner—Long V. Le
Attorney, Agent, or Firm—Brown, Martin, Haller & McClain

[57] ABSTRACT

An incubator unit has a base and a lid which are releasably securable together to define an internal sealed chamber. Inlet and outlet passageways are provided for allowing gas flow through the chamber as required. An elongate filter member is located in the outlet passageway for filtering contaminants from the gas flowing out of the chamber. One or more static filter members are mounted in the chamber at a selected height between the upper and lower walls of the chamber. The static filter member is a flat sheet of filter material held in a holder with apertures for exposing the majority of the surface of the sheet for absorbing contaminants.

11 Claims, 2 Drawing Sheets

INCUBATOR UNIT AND FILTER SYSTEM

BACKGROUND OF THE INVENTION

The present invention relates generally to incubator units or culture chambers as used for performing laboratory experiments under controlled conditions, such as culture growth, radioactive protein-labelling experiments, in vitro fertilization and the like. In such incubator units, gas concentrations, humidity and temperature can be controlled to fit experimental needs.

U.S. Pat. No. 3,886,047 of Billups, Jr. describes a relatively small culture or incubator chamber having a circular base and smoothly rounded concave lid releasably secured together by a single locking ring. One or more flat perforated trays are stacked in the chamber for supporting culture plates, culture flasks, petri dishes and the like. The chamber has an inlet and outlet for flushing with gas between experiments. This provides an inexpensive, independent incubator unit for performing experiments in isolation, eliminating cross-contamination.

When radioactive protein-labelling experiments are performed in larger, continuous flow incubators, extensive contamination problems arise. This is because radioactive $^{35}S$ gases are released in such experiments, contaminating the interior of the culture chamber and also being released into the laboratory environment, both due to exhaust of gases continuously flowing through the chamber during the experiment, and also when the chamber is opened at the end of the experiment. Thus, radioactive labelling experiments give rise to significant equipment contamination as well as air contamination, producing potential health hazards to laboratory personnel and possible contamination of subsequent experiments. It is both expensive and time consuming to decontaminate incubators using traditional techniques. Simply placing charcoal filters in the vents of incubators, as has been done in the past, will cut down on the outside air contamination but contamination within the chamber will still occur.

SUMMARY OF THE INVENTION

It is an object of the present invention to provide a new and improved incubator unit and filter system for such a unit.

According to one aspect of the present invention, an incubator unit is provided which comprises an outer housing defining an internal, sealed chamber having an upper wall and a lower wall, the housing comprising a base, a lid, and a releasable securing mechanism for releasably securing the lid to the base, the housing having inlet and outlet tubes communicating with the chamber for allowing gas flow into and out of the chamber, an elongate filter member in the outlet tube for filtering contaminants from gas flowing out of the chamber, and a static filter device in the chamber for absorbing contaminants during the experimental procedure. Preferably, the filter device comprises a floating filter member mounted in the chamber between the upper and lower walls of the chamber, and a support device for releasably mounting the floating filter member in the chamber.

In the preferred embodiment of the invention, the support device comprises a center post extending upwardly from the base of the housing, and the floating filter member comprises a filter holder having a central opening for engagement over the post and at least one flat sheet of filter material held in the filter holder. The filter holder comprises a pair of plate members each having a plurality of openings extending over their surfaces, and a securing mechanism for securing the plates together with the sheet of filter material clamped between the inner faces of the plates. Preferably, the plates have interengaging openings and projections or pins for snap engagement in the openings to secure the plates together. The plates have projections or ribs on their inner faces for clamping the filter sheet in position. This ensures that a large surface area of the filter sheet is exposed via the openings in the filter plates, for absorbing contaminants within the chamber during an experimental procedure.

More than one floating filter may be mounted on the post if necessary. The filter sheet is of charcoal paper or the like which will absorb radioactive gases. With this arrangement, a large surface area of the filter material is exposed, and this ensures that a large amount of the radioactive gases emitted during an experiment will be absorbed and will not contaminate the chamber.

The elongate filter member is preferably of activated charcoal material of the type suitable for absorbing radioactive gases and other types of contaminating gases emitted in radioactive labelling and other experiments, and is at least 2.5 inches in length. The length of the filter member is critical to ensure sufficient dwell time for substantially all radioactive contaminants to be absorbed for a given flow rate.

According to another aspect of the present invention, a method of decontaminating a culture chamber is provided which comprises the steps of placing a static filter device in the chamber along with the or each culture or petri dish, connecting a chamber outlet to an elongate filter member for filtering contaminants from gas flowing out of the chamber, connecting a chamber inlet to a supply of gas for a predetermined time period to flush gases from the chamber through the outlet filter member, sealing off the chamber inlet and outlet for a predetermined time period for performing an experimental procedure, re-connecting the inlet to the supply of gas and the outlet to the outlet filter member to flush the chamber with gas for a predetermined time period, and then opening the culture chamber to remove the experimental dishes and discarding the contaminated static filter device and elongate filter member.

Preferably, a flow meter is connected in the path of gas flowing into the chamber to control the flow rate of gases through the chamber. Additionally, a pressure release valve may be provided in the inlet flow path for venting the inlet if the pressure rises above a predetermined safety level, such as 5 p.s.i. The flow rate of gas through the chamber and the length of the elongate filter member together control the dwell or residence time of any radioactive or other contaminant gases flushed out of the chamber. Thus, the flow rate and length of the filter member can be selected to ensure that the majority of contaminants will be absorbed by the filter member. A flow rate of 5 to 7 liters of gas per minute is practical for most experimental purposes, and with this flow rate a filter member of at least 2.5 inches in length will be sufficient to absorb 99.9% or more of the radioactive gases, for most experimental purposes. If an increased flow rate is needed, for example for speedier flushing of the chamber, the outlet filter member can be made longer.

With this arrangement, volatiles released during experimental set up can be flushed from the chamber initially and absorbed in the outlet filter. At the same time, the desired mixture of gases for the particular experiment being performed can be supplied to the chamber. The chamber can then be sealed off during the experiment, avoiding the need for continuous flow through of gases as was previously necessary in a lot of cases. While the chamber is sealed, a large proportion of the released contaminants will be absorbed by the static filter inside the chamber. After completion of an experimental procedure, the chamber can be flushed a second time to remove substantially all of the remaining contaminants. The chamber can then be safely opened without risk of contaminating the laboratory, and the contaminated filters can be removed, safely discarded, and replaced with new filters prior to the next experimental procedure. This avoids the need for expensive and lengthy de-contamination procedures.

BRIEF DESCRIPTION OF THE DRAWINGS

The present invention will be better understood from the following detailed description of a preferred embodiment of the invention, taken in conjunction with the accompanying drawings, in which like reference numerals refer to like parts, and in which.

DESCRIPTION OF THE PREFERRED EMBODIMENT

Figure 1:
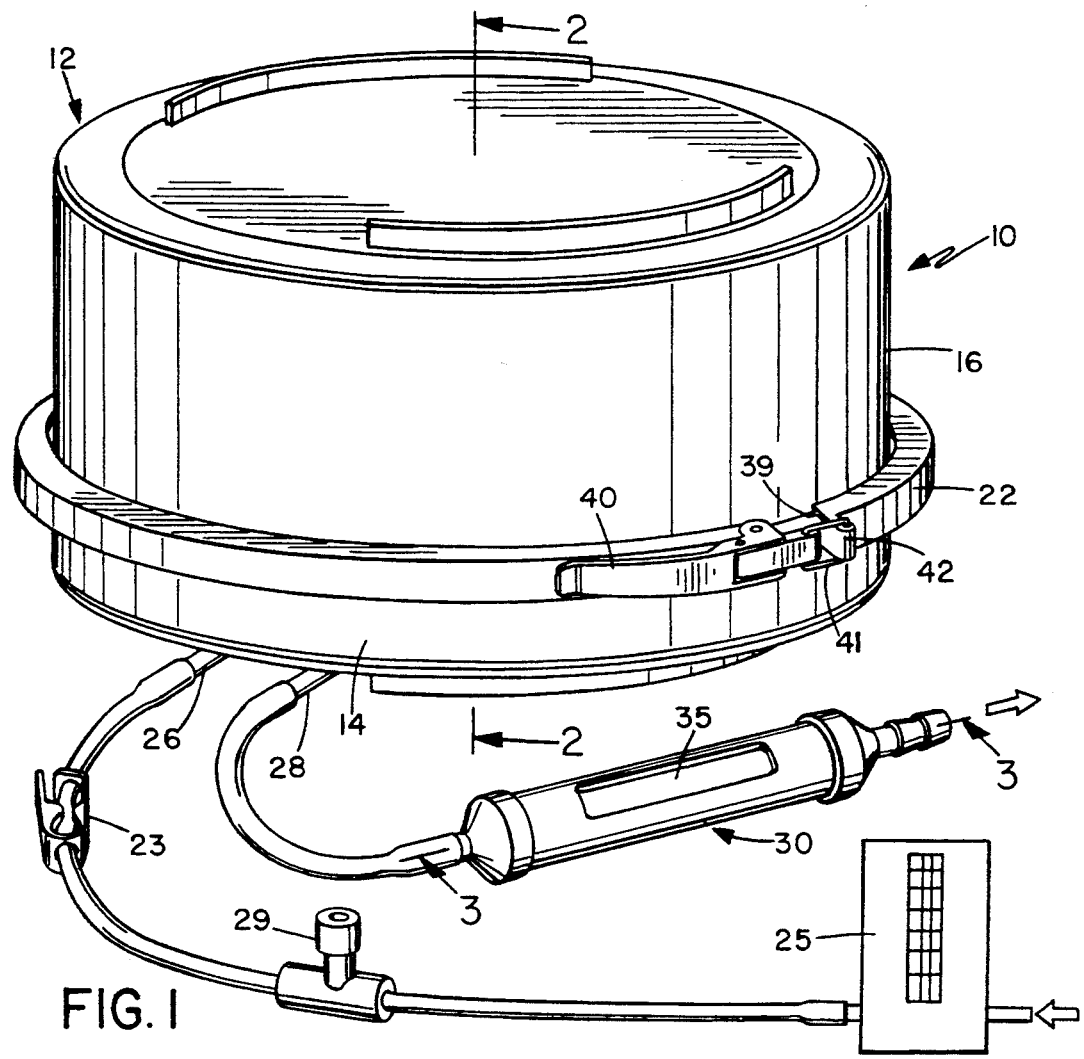
FIG. 1 is a perspective view of the complete incubator unit according to a preferred embodiment of the invention.
Figure 2:
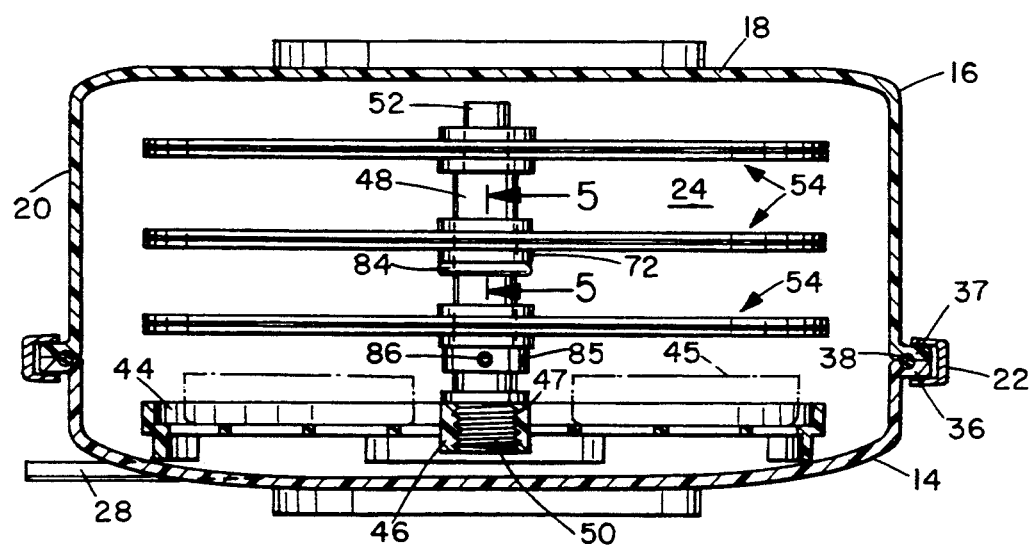
FIG. 2 is a sectional view taken on line 2—2 of FIG. 1.

An incubator unit 10 with a filter arrangement according to a preferred embodiment of the present invention is illustrated in FIGS. 1 and 2 of the drawings. The unit 10 basically comprises an outer housing 12 having a circular base 14 and a lid 16 having a matching circular upper wall 18 and downwardly depending, generally cylindrical skirt or side wall 20. The base and lid are releasably secured together via locking or clamping ring 22 to define a sealed internal chamber 24.

Figure 3:
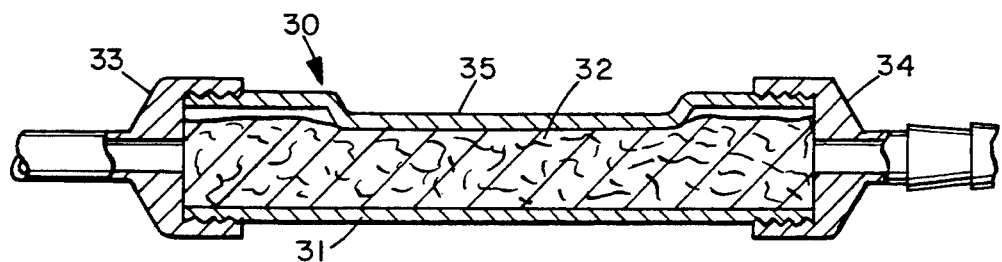
FIG. 3 is a sectional view taken of the outlet filer taken one line 3—3 of FIG. 1.

An inlet tube 26 is connected to the housing 12 for supplying gas to the chamber 24 via flow meter 25 for controlling the flow rate, and an outlet tube 28 is also connected to the housing for gas flow out of chamber 24. Suitable clamps 23 are provided for sealing off flexible portions of the inlet and outlet tubes during experimental procedures. A pressure release valve 29 is provided in the inlet tube for venting the inlet at pressures above a safety level, typically around 5 p.s.i. An outlet filter device 30 is secured to the outlet tube in the path of gas flowing out of the incubator, as illustrated in FIG. 1. The filter device 30 comprises an elongate tubular member 31 filled with filter material 32 such as activated or impregnated charcoal or the like, as best illustrated in FIG. 3. An end fitting 33 is provided at one end of the tubular member 31 for connection to outlet tubing 28, and an outlet fitting 34 is secured at the other end of the tubular member. Preferably, the tubular member 31 has an indentation 35 in its cylindrical wall which is positioned at the top of the device while the filter is in use. This ensures that there will be no continuous air gap at the top of the device even if some settling of the filter material occurs over time, as indicated in FIG. 3. The inlet and 5 outlet fittings are preferably of different sizes so that the filter device can only be connected in one orientation, to ensure gas flow in only one direction through the device.

The base and lid of the housing each have a matching annular rim 36, 37 at their upper and lower edges, respectively, which are seated against one another and secured together by locking ring 22, as best illustrated in FIG. 2. An O-ring seal 38 is clamped between the opposing faces of rims 36 and 37. The locking ring 22 comprises an annular channel member engaging over the rims 36 and 37. and having a split 39 in its periphery, with the opposing ends of the ring releasably locked together via hinged locking member 40 pivotally secured to one of the ends and releasably secured to the other end via ring 41 which engages over a hook 42 on the other end in a conventional manner.

A perforated tray 44 is seated in the base of the chamber 24, as illustrated in FIG. 2, for supporting culture dishes 45 or the like. Tray 44 has a central boss 46 with internal screw threads 47. Boss 46 supports a central post 48 which extends vertically upwardly in the chamber to a position close to the upper wall of the chamber. Central post 48 has a lower, threaded end 50 in threaded engagement with boss 46, and an upper end portion 52 of reduced diameter. Alternatively, the post may be permanently fixed in the chamber. Additional trays may be stacked on top of tray 44, in the manner described in U.S. Pat. No. 3,886,047 referred to above, if necessary. The trays will all have center openings and will be centered by post 48.

Figure 6:
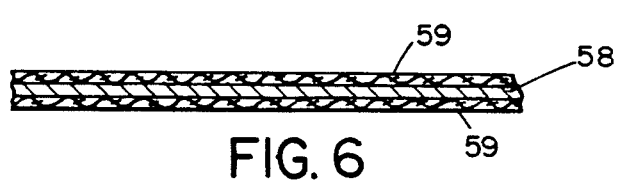
FIG. 6 is an enlarged sectional view of an alternative, multi-layer filter sheet for use in the assembly of FIGS. 4 and 5.

One or more floating filter assemblies 54 are supported at spaced intervals on post 48. One of the filter assemblies 54 is illustrated in more detail in FIGS. 3 and 4. Each filter assembly comprises a pair of perforated flat rings or holder plates 56 which are releasably secured together with a sheet 58 of filter paper such as charcoal paper clamped between the plates. Alternatively, the single sheet 58 of filter paper may be sandwiched between two sheets 59 of highly porous linen, as illustrated in FIG. 6. The rings 56 are identical, and each ring 56 has a central opening 60 for engagement over post 48, as illustrated in FIG. 4, an inner annular ring 62 surrounding opening 60, a series of radial spokes 64 with perforations or apertures 66 between the spokes 64, and outer peripheral annular ring 68.

The filter paper 58 and linen sheets 59 all have aligned central openings 61 for alignment with the openings 60 in plates 56. For ease of manufacture, the paper and linen sheets are cut out together and assembled with the plates on a centering post for easy alignment.

The inner annular ring 62 has annular ribs 70, 72 projecting from the opposite inner and outer faces of the ring around opening 60. The outer annular ring 68 has a semi-circular rib 78 projecting from its inner face, with three spaced openings 80 adjacent rib 78, and three spaced pins 82 around the remainder of the periphery of ring 68. Thus, two identical rings 56 can be releasably secured together by aligning the pins 82 on the inner face of a first ring 56 with the openings 80 on the inner face of the second ring, so that the openings 80 on the inner face of the first ring will be aligned with the pins on the inner face of the second ring. The sheet 58 of filter paper positioned between the rings, and the rings are then pressed together so that the pins snap engage in the respective aligned openings. The filter assemblies or units 54 are packaged in a sealed enclosure until needed for use, to extend shelf life.

Figure 4:
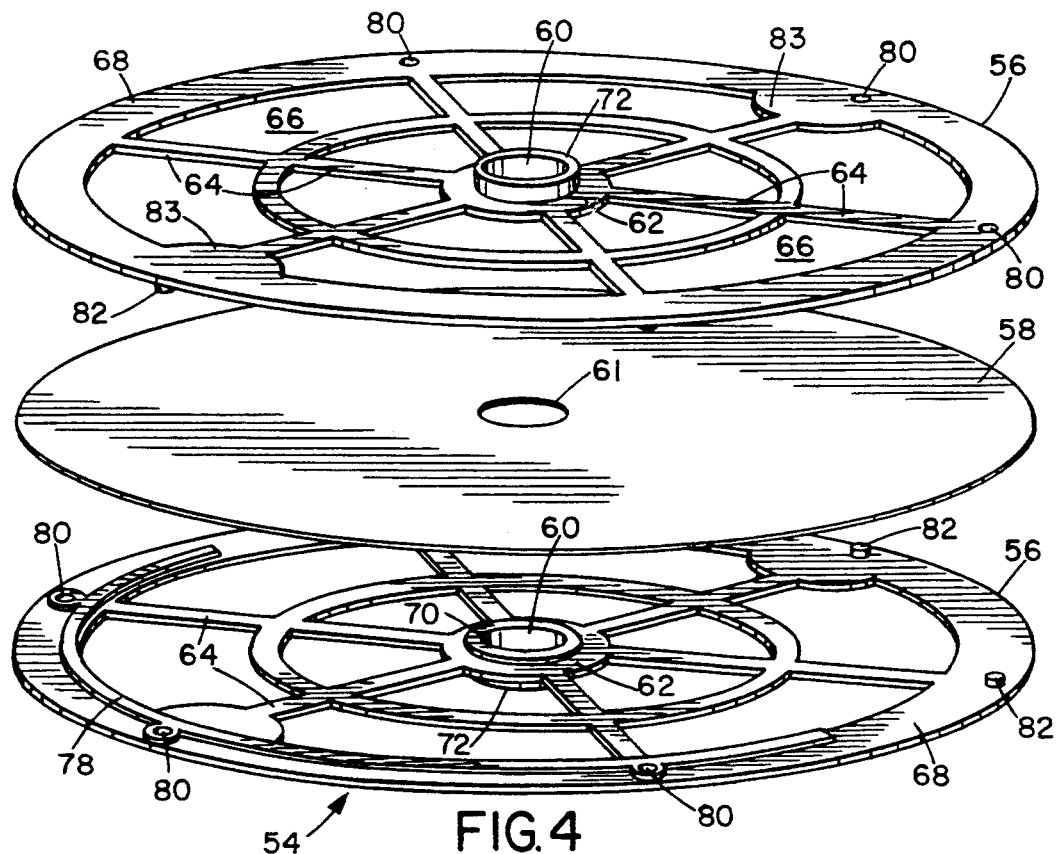
FIG. 4 is an enlarged exploded view of one filter and filter holder assembly.

The inner annular ribs 70 and outer semi-circular ribs 78 on the opposing inner faces of the two rings 56 will press against the filter paper and hold the filter paper against any movement once the rings have been snapped together, as best illustrated in FIG. 4. The filter rings are suitably made of inert plastic material or the like. This material can easily be manufactured in various colors for holding different types of filter material. Since the holder rings are identical and interchangeable, manufacture will be relatively inexpensive and assembly is very simple. The filter paper is of activated charcoal or the like which will absorb radioactive gases, and in the preferred embodiment of the invention "Activated Carbon Paper", available from Mead Corporation of South Lee, Mass., was used. The activated charcoal in this particular filter paper is formed from coconut shells, which has been found to be more effective than standard activated charcoal in absorbing radioactive gases.

The plates 56 each have diametrically opposed, arcuate projections or thumb grips 83 on their outer annular rings 68. Thumb grips 83 allow the user to pick up the unit easily without touching the paper.

Figure 5:
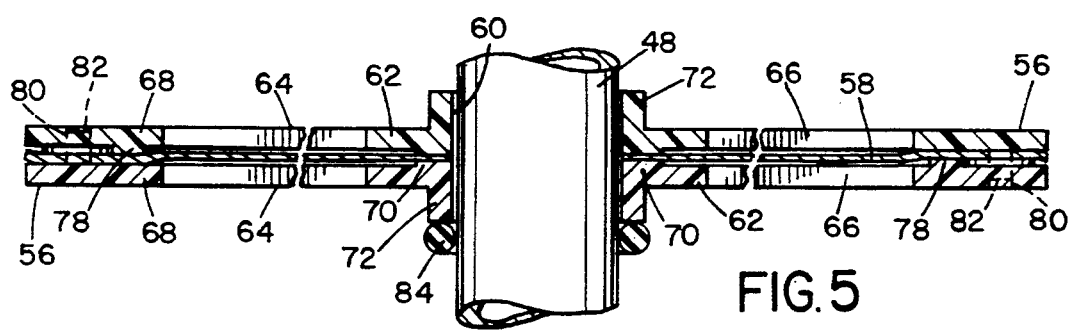
FIG. 5 is an enlarged sectional view taken on line 5—5 of FIG. 2.

The filter device is adjustably supported on the central post 48 via an O-ring 84, for example, illustrated in FIG. 5, or may alternatively be supported via an adjustable ring 85 which is releasably locked in position via set screw 86 (see FIG. 2). The filter rings 56 are of a diameter equivalent to that of tray 44, and may also be used to support culture dishes in the chamber, as illustrated in FIG. 2.

The annular projections 72 at opening 60 provide rigidity so that the filter unit does not wobble on the post. The radial webs 64 provide surface rigidity against any flexing of the plates.

The openings in the two holder rings 56 expose a substantial portion of the surface area of sheet 58 on both sides of the sheet. It has been found that the surface area of exposed filter material is more critical than the actual quantity of filter material in determining the amount of contaminants which will be absorbed, particularly in applications such as radioactive labelling where the actual mass of volatiles released is very small. This arrangement allows a relatively small amount of filter material to be used while exposing a large surface area of the material in a floating arrangement to ensure maximum efficiency. The floating support arrangement allows both surfaces of the filter paper to be exposed. In most experiments, only one filter unit 54 will be needed. However, if necessary, additional filter units 54 may be supported on post 48, so a greater surface area of filter material is provided for absorbing contaminants. Since the units are relatively small and inexpensive, waste disposal and costs are reduced.

With this filter arrangement, a large proportion of the radioactive gases or other contaminants released into the chamber in an experiment will be picked up by the filters. In order to set up an experiment using this apparatus, one or more dishes holding experimental materials are first placed on tray 44. One or two additional trays may be stacked on tray 44 if additional space is needed. One or more filter assemblies are then mounted on the post 48, with one assembly generally being sufficient for most experimental procedures. The chamber is then closed, and inlet tube 26 is connected to a supply of the gas or mixture of gases to be used as the surrounding environment during the experiment. The gas is flushed through the chamber for a predetermined time period sufficient to remove the majority of the volatiles which are released from the dish or dishes during experimental set up. The flow rate of gas can be suitably set at flow meter 25, with a flow rate of 5 to 7 liters of gas per minute generally being practical for most experimental purposes.

Once the chamber has been flushed for a sufficient time period, the inlet and outlet tubes are clamped and the chamber is then sealed off for a second predetermined time period sufficient for the experimental procedure to be completed. During the experiment, radioactive gases or other contaminants will be released into the chamber, and will tend to be picked up by the charcoal paper sheets 58. The porous linen sheets are not essential, but are desirable in order to pick up any loose carbon particles. While the experiment is performed, the outlet filter may be placed in a sealed chamber or otherwise sealed off to prevent release of any contaminants. After completion the experiment, the outlet filter is again connected to the outlet.

The flushing periods at the beginning and end of the experiment will be selected dependent on the flow rate and the predicted level of contamination. For a flow rate of 5 to 7 liters per minute, a flushing period of several minutes will be sufficient for most experimental procedures.

After completion of the experimental procedure, the clamps on the inlet and outlet tubes are again released and the chamber is again flushed with gas at the selected flow rate for a predetermined time period sufficient to remove substantially all remaining contaminating gases or volatiles. The length of the elongate, outlet filter and the flow rate are very critical in ensuring that the majority of contaminants are absorbed, since these two factors determine the dwell or residence time of gases flowing through the filter unit. Thus, the actual quantity of filter material is less critical than the length of material through which the gas travels. It has been found that a length of at least 2.5 inches is sufficient to ensure 99.9% or greater absorption of radioactive gases for most experimental purposes, at a flow rate of 5 to 7 liters; per minute. Where greater levels of radiation are encountered, or increased flow rates are necessary, the filter may be longer. Once the chamber has been flushed for a sufficient time, the gas supply is turned off, the inlet and outlet tubes are again clamped, and the lid can be opened without risk of exposure to any significant quantities of radioactive gas. The outlet filter can be changed after each experimental procedure, and the used filter units inside the chamber can be discarded and replaced with new units. This is a simple and quick procedure as compared with the lengthy and expensive cleaning, de-contamination and disposal procedures previously required.

Thus, the filter arrangement of this invention is inexpensive and convenient to use in experimental procedures where radioactive gases are released. The filter material used can be selected based on the types of radioactive nuclides released in a particular experiment. Typical filter materials for absorbing various radioactive materials include activated charcoal, T.E.D.A. (for $^{125}$I contaminants), CYPPP, and other types of charcoal.

The incubator with static and exhaust filters as described has a number of safety features and significantly reduces the risks and expense of contamination. The flow meter and pressure release valve ensure that pressure the chamber will not build up to unsafe levels. The chamber itself is also designed so that the lid will release if pressure builds up in the chamber, due to the ramped surfaces of rims 36, 37 and O-ring 38. The static filter in the chamber and the outlet filter are effective in absorbing the majority of contaminants, while being small, inexpensive, and easy to dispose of after use.

Although a preferred embodiment of the present invention has been described above by way of example only, it will be understood by those skilled in the field that modifications may be made to the disclosed embodiment without departing from the scope of the invention, which is defined by the appended claims.

I claim:

1. An incubator apparatus, comprising:
   an outer housing having an internal sealed chamber with an upper wall and a lower wall, the housing comprising a base, a lid, and a releasable securing mechanism for releasably securing the base to the lid and sealing the chamber;
   the housing having inlet and outlet passageways communicating with the chamber for allowing gas flow into and out of the chamber;
   an elongate outlet filter member in the outlet passageway for filtering contaminants from gas flowing out of the chamber;
   a static filter unit in the chamber for absorbing radioactive gases;
   the filter unit comprising a flat filter member for absorbing contaminants and a support device for releasably supporting the flat filter member at a location spaced above the lower wall and below the upper wall of the chamber; and
   the support device comprising a central post extending upwardly from the lower wall of the chamber, and the flat filter member having a central opening for sliding engagement over the central post, and mounting means for mounting the filter member at a selected height on the post.

2. The apparatus as claimed in claim 1, wherein the elongate filter member is at least 2.5 inches in length.

3. The apparatus as claimed in claim 1, wherein the elongate outlet filter and the static filter member are both of a filter material for absorbing radioactive gases.

4. The apparatus as claimed in claim 3, wherein the filter material is activated or impregnated charcoal.

5. The apparatus as claimed in claim 1, wherein the static filter member comprises at least one flat sheet of filter material having a peripheral edge and opposite faces of predetermined surface area and the support device includes holder means for holding the sheet at least around said peripheral edge while leaving a majority of the surface area on both faces of the sheet exposed, and support means for supporting the holder means in the chamber above the lower wall.

6. The apparatus as claimed in claim 5, wherein the holder means comprises a pair of flat plates each having opposite surfaces and a plurality of apertures, and interengageable securing means for securing the plates together in a face-to-face arrangement with an inner surface of each plate facing inwardly towards an opposing inner surface of the other plate and with the filter sheet held between the opposing inner surfaces of the plates.

7. An incubator apparatus, comprising:
   an outer housing having an internal sealed chamber with an upper wall and a lower wall, the housing comprising a base, a lid, and a releasable securing mechanism for releasably securing the base to the lid and sealing the chamber;
   the housing having inlet and outlet passageways communicating with the chamber for allowing gas flow into and out of the chamber;
   an elongate outlet filter member in the outlet passageway for filtering contaminants from gas flowing out of the chamber;
   a static filter unit in the chamber for absorbing contaminants;
   the static filter unit comprising a static filter member for absorbing contaminants and a support device for releasably supporting the filter member in the chamber at a location spaced above the lower wall of the chamber;
   the static filter member comprising at least one flat sheet of filter material having a peripheral edge and the support device comprising holder means for holding the sheet at least around said peripheral edge which leaving a majority of the surface area on both faces of the sheet exposed, the holder means comprising a pair of flat plates each having a plurality of apertures and interengageable securing means for securing the plates together in a face-to-face arrangement with each plate having an inner surface facing inwardly towards an opposing inner surface of the other plate and with the filter sheet held between the opposing inner surfaces of the plates;
   the support means comprising a central post extending upwardly from the lower wall of the chamber, and the plates each having a central opening for sliding engagement over the central post, and mounting means for mounting the plates at a selected height on the post.

8. The apparatus as claimed in claim 6, wherein the plates each have projecting ribs on said opposing inner surfaces for gripping the filter sheet.

9. The apparatus as claimed in claim 6, wherein one of the plates has a plurality of spaced projections on said inner surface and the other plate has a plurality of recesses on said inner surface for snap engagement with the projections on said one plate, the cooperating recesses and projections comprising said interengageable securing means.

10. The apparatus as claimed in claim 9, wherein the plates are identical and each plate has a plurality of projections and a plurality of recesses in alignment with corresponding recesses and projections, respectively, on the other plate.

11. The apparatus as claimed in claim 10, wherein the plates have a circular periphery and the projections and recesses are provided at spaced intervals adjacent the outer peripheral edge of each plate.

* * * * *